United States Patent [19]
Martin et al.

[11] Patent Number: 5,756,326
[45] Date of Patent: May 26, 1998

[54] METHOD OF TRANSFORMATION OF NOCARDIA LACTAMDURANS

[75] Inventors: Juan F. Martin; Juan-Jose R. Coque, both of Leon, Spain; C. Vasant Kumar, Hyderabad, India

[73] Assignee: Merck & Co., Inc., Rahway, N.J.

[21] Appl. No.: 888,997

[22] Filed: Jul. 7, 1997

Related U.S. Application Data

[63] Continuation of Ser. No. 741,585, Nov. 1, 1996, abandoned, which is a continuation of Ser. No. 402,784, Mar. 13, 1995, abandoned, which is a continuation of Ser. No. 205,682, Mar. 3, 1994, abandoned.

[51] Int. Cl.⁶ .......................... C12N 1/21; C12N 15/63; C12N 15/76
[52] U.S. Cl. .......................... 435/172.3; 435/252.3; 435/872
[58] Field of Search .......................... 435/172.3, 252.3, 435/872

[56] References Cited

U.S. PATENT DOCUMENTS 4,791,064  12/1988  Fare et al. .......................... 435/252.3

OTHER PUBLICATIONS

Chen, Carton W., et al., Cloning and expression of a DNA sequence conferring cephamycin C production. Biotechnology, vol. 6, Oct. 1988 pp. 1222–1224. (cumulative).

Ginther, Charles L, et al., Sporulation and the Production of Serine Protease and Cephamycin C by Streptomyces lactamdurans, Antimicrobial Agents and Chemotherapy, vol. 15, No. 4, Apr. 1979, pp. 522–526. (cumulative).

Garcia–Dominquez et al., Antimicro. Agents and Chemoth. 35(1): 44–52 (1991).

R. Coque, Juan Jose, et al., Genes for a β—lactamase, a penicillin–binding protein and a transmembrane protein are clustered with the cephamycin biosynthetic genes in *Nocardia lactamdurans*, The EMBO Journal, vol. 12 No. 2, pp. 631–639 1993. (cumulaative).

Castro, Jose M., et al., Regulation of α–aminoadiply–cysteinyl–valine, isopenicillin N synthetase, isopenicillin N isomerase and deacetoxycephalosponn C synthetase by nitrogen sources in *Streptomyces lactamdurans* Appl. Microbiol. Biotechnol. 22: pp. 32–40 1985 (cumulative).

Janssen and Bibb, Derivatives of pUC18 that have BglII sites flanking a modified multiple cloning site and that retain the ability to identify recombinant clones by visual screening of *Escherichia coli* colonies, Gene, 124 pp. 133–134 1993. (cumulative).

Kieser and Melton, Plasmid pIJ699, a multi–copy positive–selection vector for Streptomyces, Gene, 65, pp. 83–91 1988. (cumulative).

R. Coque, Juan Jose, et al., A Gene Encoding Lysine 6–Aminotransferase, Which Forms the β–Lactam Precursor α–Aminoadipic Acid, is Located in the Cluster of Cephamycin Biosynthetic Genes in *Nocardia lactamdurans*, Journal of Bacteriology vol. 173, No. 19, pp. 6258–6264 1991. (cumulative).

Matsushima and Baltz, Efficient Plasmid Transformation of *Streptomyces ambofaciens* and Streptomyces fradiae Protoplasts, Journal of Bacteriology, vol. 163, No. 1, pp. 180–185 1985. (cumulative).

Thompson, Charles et al., Cloning of Antibiotic Resistance and Nutritional Genes in Streptomycetes, Journal of Bacteriology, vol., 151, No. 2, pp. 668–677, 1982. (cumulative).

Madon and Hutter, Transformation System for Amycolatopsis (Nocardia) mediterranei: Direct Transformation of Mycelium with Plasmid DNA, Journal of Bacteriology, vol. 173, No. 20, pp. 6325–6331, 1991. (cumulative).

Lal, Rup, et al., Construction of a Hybrid Plasmid Capable of Replication in *Amycolatopsis mediterranei*, Applied and Environmental Microbiology, vol. 57, No. 3, pp. 665–671, 1991. (cumulative).

Garcia–Dominguez, Modesta, Efficient Plasmid Transformation of the β–Lactam Producer *Streptomyces clavuligerus*, Applied and Enviromental Microbiology, vol. 53, No. 6, pp. 1376–1381, 1987. (cumulative).

Murray, I.A., et al., Nucleotide sequence of the *chloramphenicol acetyltransferase* gene of *Streptomyces acrimycini*, Gene, vol 85 pp. 283–291 1989. (cumulative).

Criado, Luis M., et al., The pab gene of *Steptomyces griseu*, encoding p–aminobenzoic acid synthase, is located between genes possibly involved in candicidin biosynthesis, Gene, vol. 126 pp. 135–139, 1993. (cumulative).

Albertini, Alessandra, et al., On the Formation of Spontaneous Deletions: The importance of Short Sequence Homologies in the Generation of Large Deletions, Cell, vol. 29, pp. 319–328, 1982.

Santamaria, Ramon et al., High–Frequency Transformation of *Brevibacterium lactofermentum* Protoplasts by Plasmid DNA, Journal of Bacteriology, vol. 162, No. 1, pp. 463–467, 1985. (cumulative).

MacNeil, Douglas, Characterization of a Unique Methyl–Specific Restriction System in *Streptomyces avermitilis*, Journal of Bacteriology, vol. 170, No. 12, 1988. (cumulative).

Lechevalier, Hubert; Nocardioform Actinomycetes, Bergey's Manual of Systematic Bacteriology, vol. 4, Williams, Sharpe, and Holt (eds) Williams & Wilkins (pubs.) Baltimore, Md.) Section 26, pp. 2348–2361 1989. (cumulative).

Powell, Ian, et al., A Simple and Rapid Method for Genetic Transformation of Lactic Streptococci by Electroporation, Applied and Environmental Microbiology, pp. 655–660, 1988. (cumulative).

Lechevalier, M.P., et al., Two New Genera of Nocardioform Actinomycetes: Amycolata gen. nov. and Amycolatopsis gen. nov., International Journal of Systematic Bacteriology, vol. 36, No. 1, pp. 29–37, 1986. (cumulative).

(List continued on next page.)

*Primary Examiner*—Johnny F. Railey, II
*Attorney, Agent, or Firm*—Michael D. Yablonsky; Jack L. Tribble

[57] ABSTRACT

A method is disclosed for the high efficiency transformation of species of the genus Nocardia with DNA molecules. DNA vectors for the transformation of genes into Nocardia as well as recombinant Nocardia host cells expressing recombinant genes are disclosed.

4 Claims, 6 Drawing Sheets

OTHER PUBLICATIONS

Wesseling and Lago, Strain Improvement by Genetic Recombination of Cephamycin Producers, *Nocardia lactamdurans* and *Streptomyces griseus*, Developments Ind. Microbiol., vol. 22, pp. 641–651 1981. (cumulative).

Stapley, E.O., et al., Cephamycins, a New Family of B–Lactam Antibiotics, Antimicrobial Agents and Chemotherapy, vol. 2, No. 3, pp. 122–131 1972. (cumulative).

Coque, J.J., et al., The Cephamycin biosynthetic genes pcbAB, encoding a large multidomain peptide synthetase, and pcbC of *Nacardia lactamdurans* are clustered together in an organization different from the same genes in Acremonium chrysogenum and Penicillium chrysogenum, Molecular Microbiology, vol. 5, (5) pp. 1125–1133, 1991. (cumulative).

Clayton and Bibb, Streptomyces promoter–probe plasmids that utilise the xylE gene of Pseudomonas putida, Nucleic Acids Research, vol. 18, No. 4, pp. 1077, 1989.

Kieser, Tobias, et al., pIJ101, a Multi–Copy Broad Host–Range Streptomyces Plasmid: Functional Analysis and Development of DNA Cloning Vectors, Mol. Gen. Genet. vol. 185, pp. 223–238, 1982. (cumulative).

Martin, J.F., Cloning Systems in Amino Acid–producing Corynebacteria, Biotechnology, vol. 5, pp. 137–146, 1987. (cumulative).

Dunican and Shivnan, High Frequency Transformation of Whole Cells of Amino Acid Producing Coryneform Bacteria Using High Voltage Electroporation, Biotechnology, vol. 7, pp. 1067–1070, 1989. (cumulative).

Martin, Juan F., Clusters of genes for the biosynthesis of antibiotics: regulatory genes and overproduction of Pharmaceuticals, Society for Industrial Microbiology, vol. 9, pp. 73–90, 1992. (cumulative).

Santamaria, Ramon, et al., Characterization of an Endogenous Plasmid and Development of Cloning Vectors and a Transformation System in *Brevibacterium lactofermentum*, Journal of General Microbiology, vol. 130, pp. 2237–2246, 1984. (cumulative).

Castro, Jose M, et al., Purification and Characterization of the Isopenicillin N Synthase of *Streptomyces lactamdurans*, Journal of General Microbiology, vol., 134, pp. 133–141, 1988. (cumulative).

Cortes, Jesus, et al., Purification and Characterization of a 2–Oxoglutarate–linked ATP–independent Deacetoxycephalosporin C Synthase of *Streptomyces lactamdurans*, Journal of General Microbiology, vol. 133, pp. 3165–3174, 1987. (cumulative).

Laiz, Leonila, et al., Purification and Characterization of the isopenicillin N epimerase from *Nocardia lactamdurans*, Journal of General Microbiology, vol. 136, pp. 663–671, 1990.

Katz, Edward, et al., Cloning and Expression of the Tyrosinase Gene from Streptomyces antibioticus in *Streptomyces lividans*, Journal of General Microbiology, vol. 129, pp. 2703–2714, 1983(cumulative).

Kieser, Tobias, Factors Affecting the Isolation of CCC DNA from *Streptomyces lividans* and *Escherichia coli*, Plasmid, vol. 12, pp. 19–36, 1984, (cumulative).

Coque, Juan Jose, et al., Characterization and expression in *Streptomyces lividans* of cefD and cefE genes from Nocardia lactamdurans: the organization of the cephamycin gene cluster differs from that in *Steptomyces clavuligerus*, Mol. Gen. Genet. vol. 236, pp. 453–458, 1993. (cumulative).

Matushima et al. Efficient Transformation of Amycolatopsis orientalis (*Nocardia orientalis*) Protoplasts by Streptamyces Plasmids, J. of Bacteriology, May 1987 pp. 2298–2300. (cumulative).

Maniatis et al. Molecular Cloning, A Laboratory Manual, Cold Spring Harbor Laboratory p. 4, 1982, (cumulative).

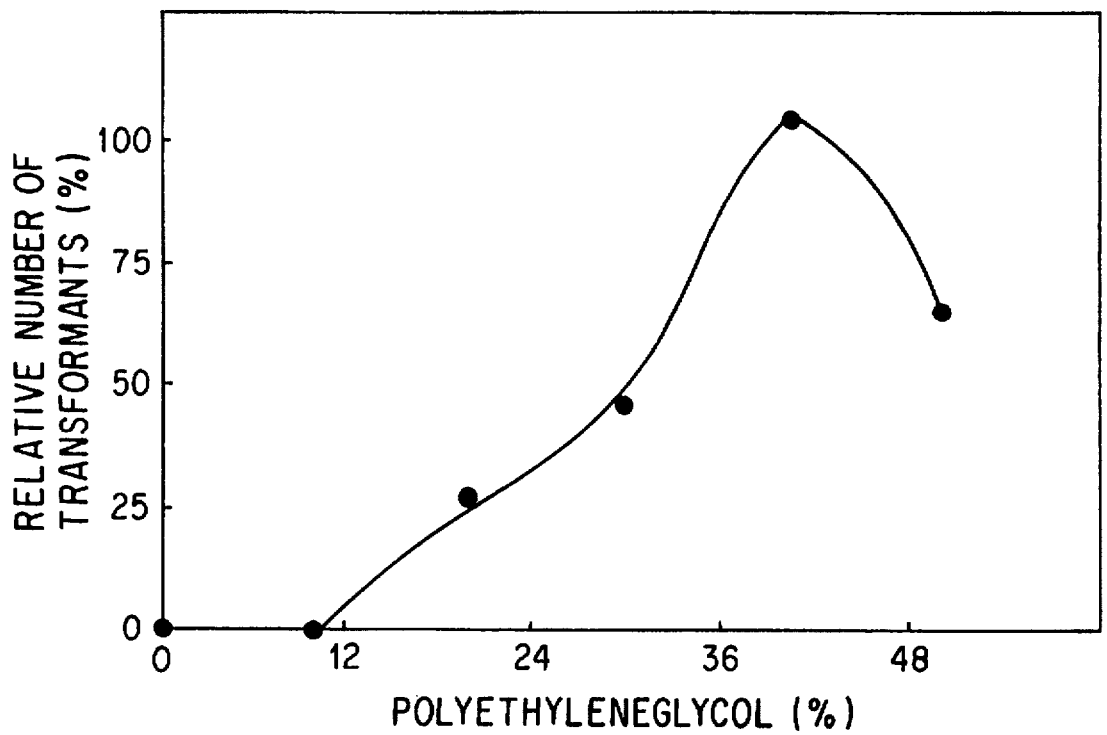
F I G. 2A
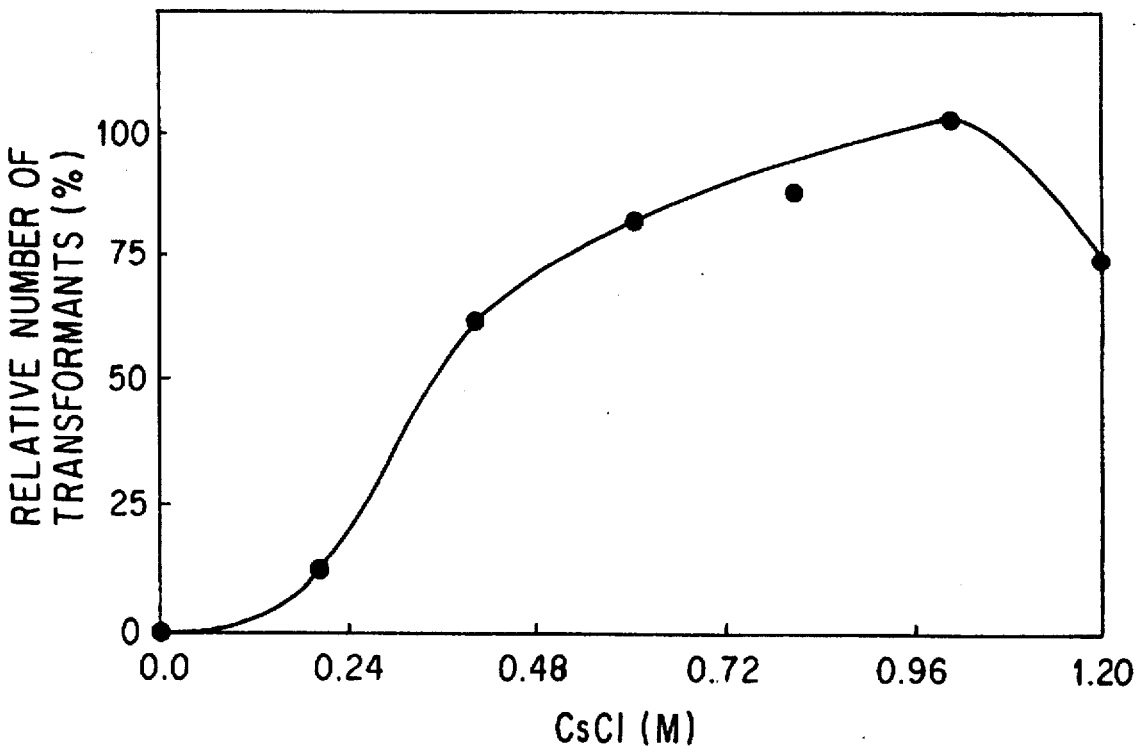
F I G. 2B

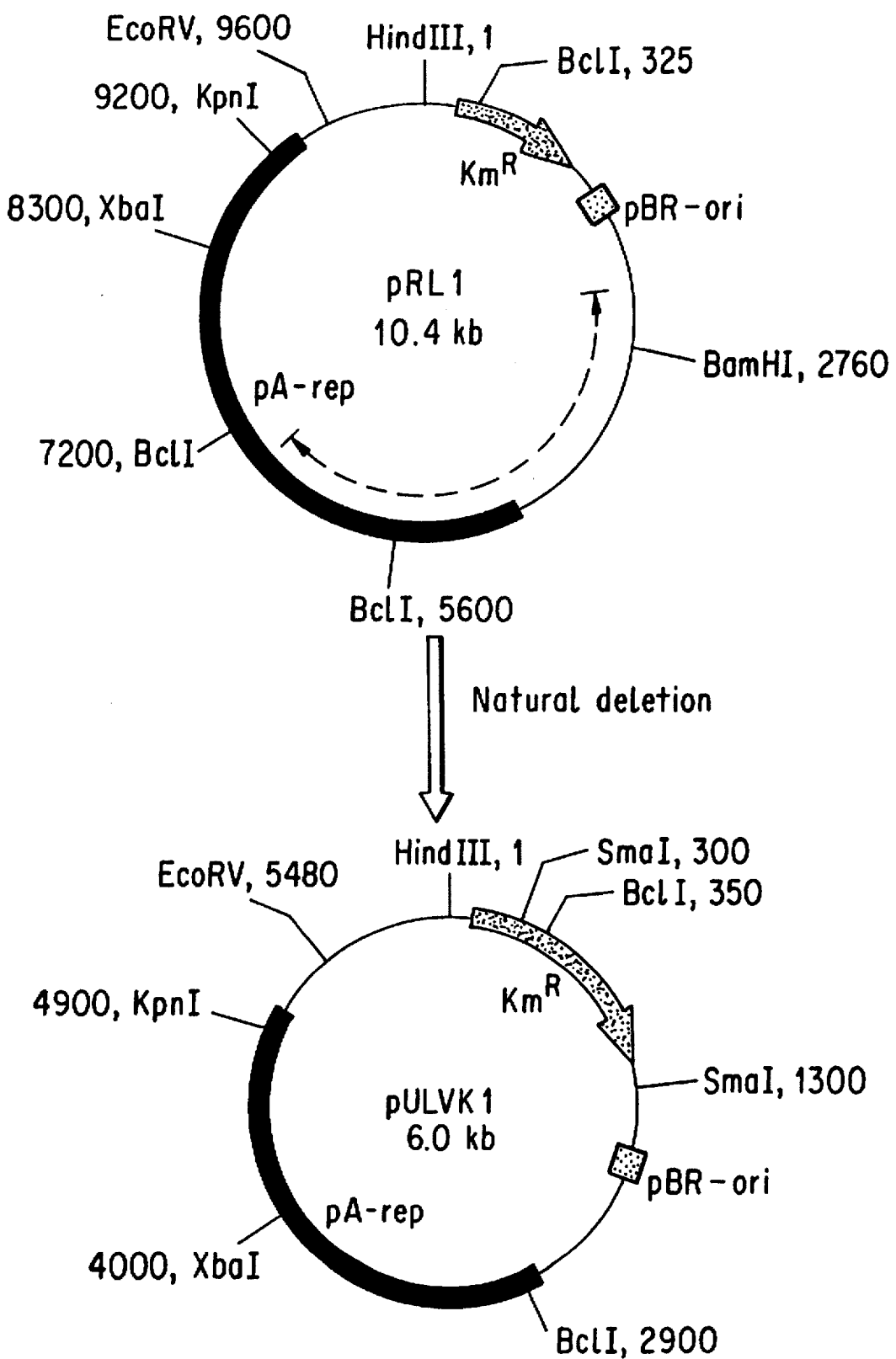
F I G. 3

METHOD OF TRANSFORMATION OF NOCARDIA LACTAMDURANS

This is a continuation of Ser. No. 08/741,585, filed Nov. 01, 1996, abandoned, which is a continuation of Ser. No. 08/402,784, filed Mar. 13, 1995, abandoned, which is a continuation of Ser. No. 08/205,682, filed Mar. 3, 1994, abandoned.

BACKGROUND OF THE INVENTION

Several species of Nocardia and the related genus Amycolatopsis are used industrially for the production of antibiotics. Nocardia lactamdurans (Wesseling and Lago, 1981, Developments Ind. Microbiol., 22, pp 641–645) (previously described as Streptomyces lactamdurans, Stapley et al., 1972 Antimicrob. Agents Chemother., 2, pp 122–131) produces the β-lactam antibiotic cephamycin C (Castro et al., 1985, Appl., Microbiol., Biotechnol., 22, pp 32–40; Cortés et al., 1987, J. Gen. Microbiol., 133, pp 3165–3174) and the polyether efrotomycin. Nocardia mediterranei (recently renamed Amycolatopsis mediterranei) (Lechevalier et al., 1986, Int., J. Syst., Bacteriol 36, pp 29–37) produces rifamycin and A. orientalis synthesizes vancomycin. The biosynthetic pathway of cephamycin in N. lactamdurans has been extensively studied (Castro et al., 1988, J. Gen., Microbiol., 134, pp 133; Cortés et al., 1987 supra; Laiz et al., 1990, J. Gen., Microbiol, 136, pp 663–671) and the cluster of the cephamycin biosynthetic pathway has been cloned (Coque et al ., 1991, mol. Microbiol., 5, pp 1125–1133; Coque et al., 1991, J. Bacteriol., 173, pp 6258–6264; Coque et al., 1993, Mol. Gen. Genet., 236, pp 453–458; Coque et al., 1993, EMBO J., 12, pp 631–639). However, the difficulty to transform N. lactamdurans has hampered further studies on gene disruption and gene amplification.

N. lactamdurans could not be transformed with vectors based on Streptomyces replicons. Since no endogenous circular plasmids occur in N. lactamdurans replicons from different bacteria related to the Nocardia group, e.g. corynebacteria, Rhodococcus fascians, Amycolatopsis sp and Streptomyces lividans were studied. Polyethylene glycol-assisted transformation of protoplasts (Hopwood et al., 1985 J. Gen. Microbiol., 129, pp 2703–2714) and electroporation have been widely used for transformation of Streptomyces. Another method which uses a combination of polyethylene glycol and alkaline cations to transform cells of A. mediterranei was developed by Madon and Hutter (1991) J. Bacteriol., 173, pp 6325–6331.

The current processes for cephamycin production on an industrial scale rely on non-recombinant microbial synthesis systems without the advantages conferred by genetic manipulation of the cephamycin producing organism.

BRIEF DESCRIPTION OF THE DRAWINGS

FIG. 3 Formation of the stable plasmid pULVK1 by natural deletion in N. lactamdurans LC411 of plasmid pRL1 is shown; thin line: DNA originating from E. coli plasmids carrying the pBR322 origin of replication (pBR-ori) and the kanamycin resistance gene from Tn5 ($Km^R$); thick line: DNA from Amycolatopsis sp. containing the pA387 origin of replication (pA-rep); the dashed arc indicates the fragment of DNA which is deleted to form pUVK1.

SUMMARY OF THE DISCLOSURE

Figure 1:
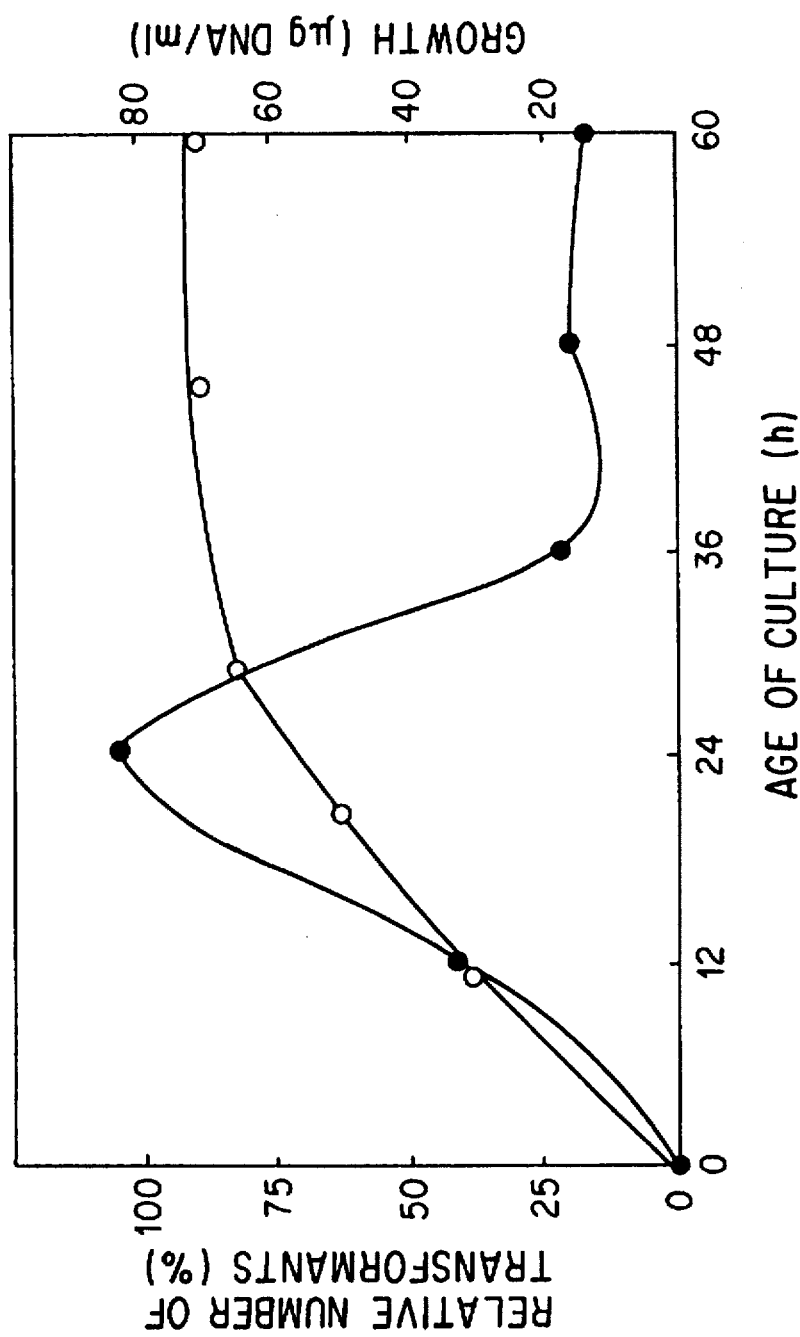
FIG. 1 Effect of the age of N. lactamdurans culture in NYG medium on the efficiency of transformation; growth as µg of cellular DNA per ml (o); number of transformants relative to the best transformation conditions (1) ($2 \times 10^5$ transformants per µg of DNA was considered as 100%).

High transformation efficiency (about 1 to $7 \times 10^5$ transformants per µg of DNA) of Nocardia was obtained by direct treatment of mycelium with polyethylene glycol and cesium chloride. A variety of vectors from Streptomyces lividans, Brevibacterium lactofermentum, Rhodococcus fasicans and Nocardia (Amycolatopsis) sp. were tested; transformants were obtained with vectors derived from an endogenous plasmid of the strain Amycolatopsis DSM 43387. Vectors were constructed carrying the kanamycin resistance gene (kan) as selective marker. The transformation procedure was optimized using one of these vectors (pULVK1) by studying the influence of the age of culture, concentrations of cesium chloride and polyethylene glycol, amount of plasmid DNA, and nutrient supplementations of the growth medium. Versatile bifunctional cloning vectors (pULVK2, pULVK3) were developed by subcloning a multiple cloning site, or a synthetic polylinker containing several unique restriction sites (coRV, DraI, BamHI, EcoRI and HindIII). A second marker, the apramycin resistance gene (amr) was added to the vectors (pULKVK2A) allowing insertional inactivation of one of the markers while using the second marker for selection. An alternative marker, the amy gene of Streptomyces griseus, was added (PULAM2) which is easily detected by the release of extracellular amylase in transformants carrying this vector. Two promoter probe plasmids pULVK4 and pULVK5 have been constructed, using the promoterless xy1E gene as reporter.

DETAILED DESCRIPTION OF THE INVENTION

Methods for efficient transformation of S. lividans and several other species of Streptomyces have been developed (Thompson et al., 1982 J. Bacteriol., 151, pp. 668–677; Matsushima and Baltz, 1985 J. Bacteriol., 163, pp. 180–185). However transformation of many species of Steptomyces and other rare actinomycetes of industrial relevance had not been achieved. Efficient plasmid transformation of the β-lactam producer S. clavuligerus has been developed (García-Dominguez et al., 1987 Appl. Environm. Microbiol., 53, pp. 1376–1381), but repeated attempts to transform the cephamycin C producer N. lactamdurans using Streptomyces vectors were unsuccessful since plasmids containing origins of replication from *S. lividans, R. fascians* or *B. lactofermentum* do not transform *N. lactamdurans*. The present invention discloses the successful transformation of *N. lactamdurans* using vectors derived from the endogenous *Amycolatopsis* sp DSM43387 plasmid pA387 (plasmid pA387 is described by Lal et al., 1991 Appl. Environm. Microbiol., 57, pp. 665–671). Successful transformation of Nocardia species using the vectors of the present invention is of great interest since the genera Nocardia and Amycolatopsis appear to be closely related (Lechevalier, 1989 In: Bergeys Manual of Systematic Bacteriology, Vol. 4; Williams, Sharpe, and Holt (eds) pp. 2348–2361, Williams and Wilkins, Baltimore, Md).

Polyethylene glycol (PEG)-assisted transformation of protoplasts is well known. The lack of transformation of *N. lactamdurans* protoplasts even with pULVK1 (described below) appears to be related to the poor DNA uptake of *N. lactamdurans* protoplasts. Regeneration of the complex cell wall of *N. lactamdurans* protoplasts might be incomplete, as described also for regeneration of corynebacteria protoplasts apparently due to the need of synthesizing mycolic acids (Martín et al., 1987 Bio/Technology, 5, pp. 137–146).

Electroporation has proved to be useful for transformation of bacteria for which alternative DNA transfer methods did not exist or were inefficient. Electroporation had been applied to transformation of corynebacteria (Dunican and Shivnan, 1989 Bio/Technology, 7, pp. 1067–1070) and lactic acid bacteria (Powell et al., 1988 Appl. Environm. Microbiol., 54, pp. 655–660). The inefficient transformation of *N. lactamdurans* by electroporation prompted us to try direct transformation of entire cells with polyethylene glycol and alkaline cations, a method reported for transformation of *Amycolatopsis mediterranei* (Madon and Hutter, 1991 J. Bacteriol., 173, pp. 6325–6331). In this method the mycelium does not need any special preparation and the critical steps of protoplast regeneration are avoided.

Several factors were optimized to get high efficiencies of transformation. The age of the culture was critical to get a good transformation efficiency. Efficient transformation was observed during a period of about 20 hours between approximately 20 hours and 40 hours of logarithmic growth. The preferred efficiency was obtained at about 24 hours when the cells are in the logarithmic phase of growth and decreased after about 40 hours probably due to the modification of the cell wall or to the formation of nucleases. In *S. clavuligerus* a similar effect of the cell growth phase on protoplast transformation was observed (García-Dominguez et al., 1987 supra).

The source of plasmid DNA used in transformation was important for successful electroporation of *N. lactamdurans*. A 40 to 80-fold increase in the efficiency of transformation was obtained when plasmid DNA was isolated from a dam-, dcm- strain of *E. coli* instead of *E coli* DH5α, which indicates that the different methylation of the plasmid DNA from *E. coli* as compared to the normal modification in Nocardia is responsible for the low efficiency of initial transformation. This problem was avoided by the use of an *E. coli* dam- dcm- strain or by isolating plasmid DNA directly from previously transformed *N. lactamdurans*. Strains of *E. coli* which are dam- dcm- are commercially available and include but are not limited to JMI 110. The presence of DNA restriction system in *N. lactamdurans* may explain the low transformation efficiency obtained by using DNA from heterologous hosts. In fact, a methyl-specific restriction system has been found in the actinomycete *Streptomyces avermitilis* (MacNeil, 1988 J. Bacteriol., 170, pp. 5607–5612) and similar restriction systems are likely to occur in many other actinomycetes.

One important finding was the observation of the deletion of a constant 4.0 kb fragment from plasmid pRL1 which gave rise to the stable plasmid pULVK1. A similar deletion of unstable corynebacterial plasmid pULRS61 which originated the stable plasmid pUL330 and 340 was found in *B. lactofermentum* (Santamaría et al., 1984 J. Gen. Microbiol., 130, pp. 2237–2246; Santamaría et al., 1985 J. Bacteriol., 162, pp. 463–467). Such deletions occur frequently with plasmids that contain short repeats of a certain sequence (Albertini et al., 1982 Cell, 29, pp. 319–328; Murray et al., 1989 Gene, 85, pp. 283–291; Criado et al., 1993 Gene, 126, pp. 135–139) or that replicate via the rolling circle mechanism (Fernández et al, 1994). The deleted plasmid pULK1 gave very high efficiencies of transformation (up to $2\times10^5$ transformants per μg of DNA) as compared to the undeleted pRL1 form which indicates that many cells transformed with the undeleted form were probably unable to replicate the plasmid in an stable form and it was lost from the cells.

The copy number of pULVK1 that was observed (20–30 copies/cell) is lower than the copy number reported for pRL1 (about 90 copies/cell) (Lal et al., 1991 supra) possibly due to less recognition of the origin or replication of the *Amycolatopsis* sp. plasmid by the *N. lactamdurans* plasmid replication machinery. The stable plasmid pULVK1 has served as the starting point to construct a variety of plasmids with two selective markers (FIGS. 3 and 4) and promoter-probe vectors (FIG. 5) for use in *N. lactamdurans*. These vectors are very useful instruments for advanced molecular genetics applications of *N. lactamdurans*. A variety of selective markers are suitable for use in the present invention. Suitable selectable markers are known in the art and include but are not limited to kanamycin resistance gene, thiostrepton resistance gene, erythromycin-resistance gene, apramycin resistance gene and phleomycin-resistance gene. In addition, a variety of promoters are suitable for use in the present invention for expression of recombinant genes. Suitable promoters include but are not limited to the tip (thiostrepton induced protein) promoter, the kan (kanamycin-resistance gene) promoter, the cefD (isopenicillin N epimerase) promoter, and the mel (melanine biosynthesis) promoter. While the microorganism *N. lactamdurans* is used to demonstrate the present invention, it is readily apparent to those of ordinary skill in the art that other species of Nocardia are suitable for use. Other species of Nocardia include but are not limited to *Nocardia amarae*, *Nocardia brevicatena*, *Nocardia carnea*, *Nocardia cellulans*, *Nocardia* (*Amycolatopsis*) *mediterranei*, and *Nocardia* (*Amycolaptosis*) *orientalis*.

The following examples are provided as illustrative of the present invention without however, limiting the same thereto.

EXAMPLE 1

Selection of antibiotic resistance markers

The sensitivity of *N. lactamdurans* to different antibiotics was tested in S27M (Madon and Hutter, 1991 supra) or modified ELR medium (Wesseling and Lago, 1981 supra). *N. lactamdurans* was resistant to hygromycin and viomycin (MIC higher than 100 μg/ml) or chloram-phenicol (MIC higher than 75 μg/ml) but it was sensitive to thiostrepton (5 μg/ml) phleomycin (15 μg/ml), kanamycin (30 μg/ml) or apramycin (25 μg/ml). Thiostrepton-resistant mutants appeared spontaneously with high frequency. Therefore, the thiostrepton resistance (tsr) marker was not used. In addition, thiostrepton is known to have multiple regulatory effects on *N. lactamdurans* and other actinomycetes (Kumar et al., 1993; García-Domínguez et al., 1991 Antimicrob Agents Chemother., 35, pp. 44–52). Although Nocardia is sensitive to phleomycin, the antibiotic cannot be used for primary selection since it appears that components of S27M medium affects the antibiotic activity. Kanamycin was used as the first selective marker because of the high level of resistance that was conferred by the kan gene of transposon Tn5 and the availability of the antibiotic. Apramycin or pheleomycin resistance genes were used as secondary markers. The unique XhoI site in the amr gene can be used for cloning XhoI compatible fragments what results in the insertional inactivation of this selective marker.

EXAMPLE 2
Transformation procedure

A seed culture of *N. lactamdurans* LC 411, a stable variant isolated from the wild type NRRL 3802 was grown by inoculating 1.5 ml of stock cell suspension (in 20% glycerol) into NYG medium [Ginther, C. L., 1979, Antimicrob. Agents Chemother., 15, pp. 522–526] supplemented with 0.85% $MgCl_2$, and incubated for 36 hours at 30° C. and 250 rpm in an orbital shaker. After growth, 5 ml of this culture were used to inoculate 100 ml of the same medium containing 0.1% Tween 80 in 500 ml baffled Erlenmeyer flasks, and the incubation was carried out in the same conditions. Cells (10 ml aliquots) were collected at different times by centrifugation, resuspended in 5 ml of 20% glycerol and preserved at −20° C. until use.

For transformation, cells were pelleted by centrifugation, washed twice with the same volume of sterile TE buffer [20 mM TRIS, ImM EDTA, pH8.0], and finally with a 25 mM TRIS-HCl (pH 8.0) solution, and then resuspended in one tenth of the original volume in the same buffer. The transformation mixture consisted of 50 µl of 4M CsCl; 1 µl of 1M $MgCl_2$; 5.0 µl of sonicated calf thymus DNA (5 µg/µl) and plasmid DNA in 2.5 µl volume. The total volume was made up to 100 µl by adding the *N. lactamdurans* cell suspension. After that, 100 µl of 80% PEG 1000 (Khock Light, UK) were added to a final concentration of 40%. The components of the transformation mixture were mixed carefully by pipetting up and down, incubated at 30° C., for 1 hour, and then at 42° C. for 10 minutes.

After the incubation, aliquots of the transformation mixture were plated onto S27M media plates (Madon and Hutter, 1991), previously dried in a hood for about 2 to 3 hours, by mixing the transformed cells with 2–3 ml of an overlay of melted R2L agarose (0.7%). PEG elimination from the transformation mixture is not required, since it is not toxic for the microorganisms and does not have any influence on the final result of the transformation. In some experiments the transformation mixture was diluted in R2L liquid medium [or in P buffer (Hopwood et al., 1985)] and then plated in the same way.

Plates were briefly dried before they were incubated at 30° C. Kanamycin (75 µg/ml in water solution) or apramycin (50 µg/ml) was added after 20 hours of incubation. Transformants began to appear about 72 to 96 hours after adding the antibiotic. Single colonies were picked up for further analysis.

Electroporation

Cells grown in NYG medium as indicated above were harvested at different times and then washed 5 times with milli-Q sterile water and finally resuspended in one fiftieth of the original volume and preserved in aliquots until use. Cell suspensions (75 µl aliquots) were mixed with 1–2 µl of plasmid DNA and then transferred into a chilled electroporation cuvette, and exposed to a single pulse of varying field strengths (5 to 12.5 kv/cm) and pulse duration from 2.3 to 6.6 milliseconds in a BioRad apparatus. After electroporation, cells were added to 0.5 ml of NYG medium and incubated with agitation at 30° C. for about 3–6 hours and then plated onto plates containing the antibiotic (kanamycin, 75 µg/ml or apramycin, 50 µg/ml).

EXAMPLE 3
Protoplast transformation and electroporation

Initially, transformation of *N. lactamdurans* protoplasts was tried with vectors pIJ702 or pIJ699 from *S. lividans* (Hopwood et al., 1985 supra; Matsushima et al., 1987 supra), pUL340, pULRS8 and pULMJ600 of *B. lactofermentum* (Santamaría et al., 1984 supra; 1985 supra; Martín et al, 1990 pp. 283–292, In: Proceeding Of The 6th International Symposium on Genetics of Industrial Microorganisms, Heslot, Davies, Florent, Robichon, Durand and Penasse (eds), Societé Francaise de Microbiologie, Paris), pRL1 of *Amvcolatopsis* sp. and pULRE1, pULRE2 ands pULRE3 of *Rhodococcus fascians*. No transfonnants were obtained with any of the plasmids probably due to the inability of these plasmids to replicate in *N. lactamdurans* or to the low efficiency of protoplast DNA uptake, although *N. lactamdurans* can be easily protoplasted and regenerated in the modified ELR or S27M media described for this purpose.

A variety of electroporation conditions (with the same plasmids) were tested by varying the field strength from about 5 to 12.5 kv/cm and pulse duration from about 2.3 to 6.6 milliseconds. The results of the electroporation were very poor (0.1–1 transformants per µg of DNA) with plasmid pRL1 and did not improve by growing the cells in presence of glycine (0.5–1%) and/or Tween-80, or by pretreatment of the mycelium with lysozyme (100 µg/ml) for 5 min. No transformants were obtained after electroporation with plasmids from corynebacteria, *R. fascians* or *S. lividans*.

EXAMPLE 4
Initial polyethylene glycol and cesium chloride assisted transformation of intact cells A successful transformation of *N. lactamdurans* with plasmid pRL1 obtained from *E. coli* DH5α was obtained when intact cells were incubated with plasmid DNA in presence of polyethylene glycol and CsCl. The low initial efficiency (1 to 10 transformants per µg of DNA) was significantly increased (40–80 transformants per µg of DNA) when pRL1 was obtained from *E. coli* JM110 (a dam-, dcm-strain) instead of *E. coli* DH5α.

The age of the *N. lactamdurans* culture was very important to get the highest transformation efficiencies. Two to five-fold higher efficiencies (up to about 400 transformants per µg of DNA) were obtained by using 24 hour mycelium than when 36 hour old mycelium was used. Cells from cultures of about 48–72 hours were more difficult to transform (FIG. 1) but transformants were obtained nonetheless. The best efficiency of transformation was obtained when the culture was in the exponential phase of growth, about 8 to 10 hours before the organism reaches the stationary phase.

EXAMPLE 5
Optimization of polyethylene glycol, cesium chloride, Tween 80 and DNA concentrations Initial studies indicated that growth of *N. lactamdurans* in NYG medium supplemented with $MgCl_2$ (8.5 g/l) and Tween −80 (0.1%) supported a higher transformation efficiency than TSB with the same added components. Other compounds such as glycine (0.5–1%) (a known inhibitor of cell wall biosynthesis), alone or in combination with Tween-80, and/or $MgCl_2$ always yielded a lower number of transformants.

The addition of PEG to the transformation mixture was strictly required. No transformants were obtained in the absence of PEG. A good transformation efficiency was obtained in a narrow range of PEG 1000 concentration (from about 30–48%); the optimal efficiency was consistently observed at about 40% PEG (FIG. 2A).

Another important factor to obtain efficient transformation was the CsCl concentration. Relatively high concentrations of CsCl (above about 0.4M) were required. The optimal efficiency of transformation was observed at about 1M concentrations of this salt, although a high number of transformants was also obtained at lower or higher CsCl concentrations (FIG. 2B). Substitution of CsCl either by RbCl, LiCl or KCl at 1M concentration, yielded only 36% (for RbCl) or 0% (for KCl or LiCl) of the transformants obtained with CsCl (Table 1). Likewise substitution of $Mg^{2+}$ mby $Ca^{2+}$ at the same concentration (about 1M) yielded about 30–40% transformants as compared to control transformations with $Mg^{2+}$.

TABLE 1

Effect of different alkaline salts on the transformation of cells of N. lactamdurans

| Alkaline salts | Efficiency of transformation | |
|---|---|---|
| | Number of transformants/μg DNA | % |
| CsCl 1M | $6.7 \times 10^5$ | 100 |
| RbCl 1M | 0 | 0 |
| LiCl 1M | $2.4 \times 10^5$ | 36 |
| KCl 1M | 0 | 0 |
| CsCl 1M, $CaCl_2$ 0.1M (substituting for $MgCl_2$ 0.1M) | $2.6 \times 10^5$ | 38 |

0.1M $MgCl_2$ was used in all experiments except in the last transformation in which it was replaced by 0.1M $CaCl_2$.

Figure 2C:
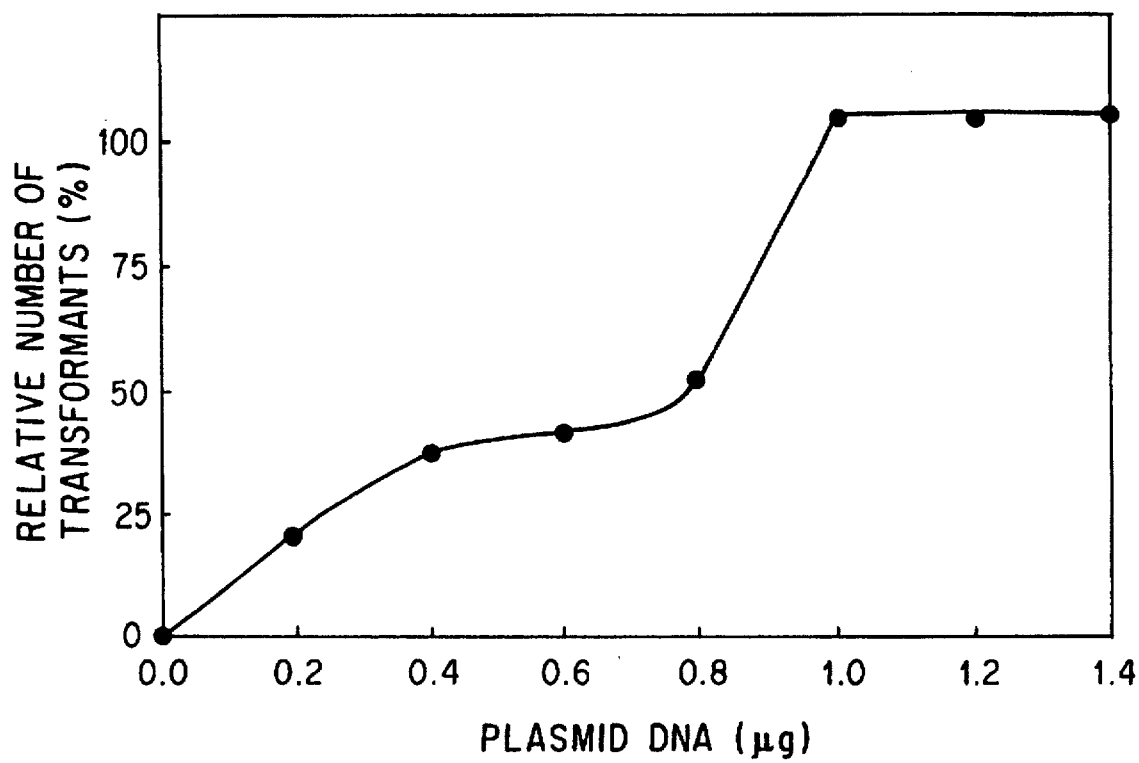
FIG. 2 Panels A–D Optimization of different parameters affecting the efficiency of transformation; Panel A, Concentration of polyethylene glycol 1000; Panel B, Concentration of CsCl; Panel C, Concentration of plasmid DNA (pULVK1) per transformation experiment; Panel D, Concentration of competing (calf thymus) DNA.
Figure 2D:
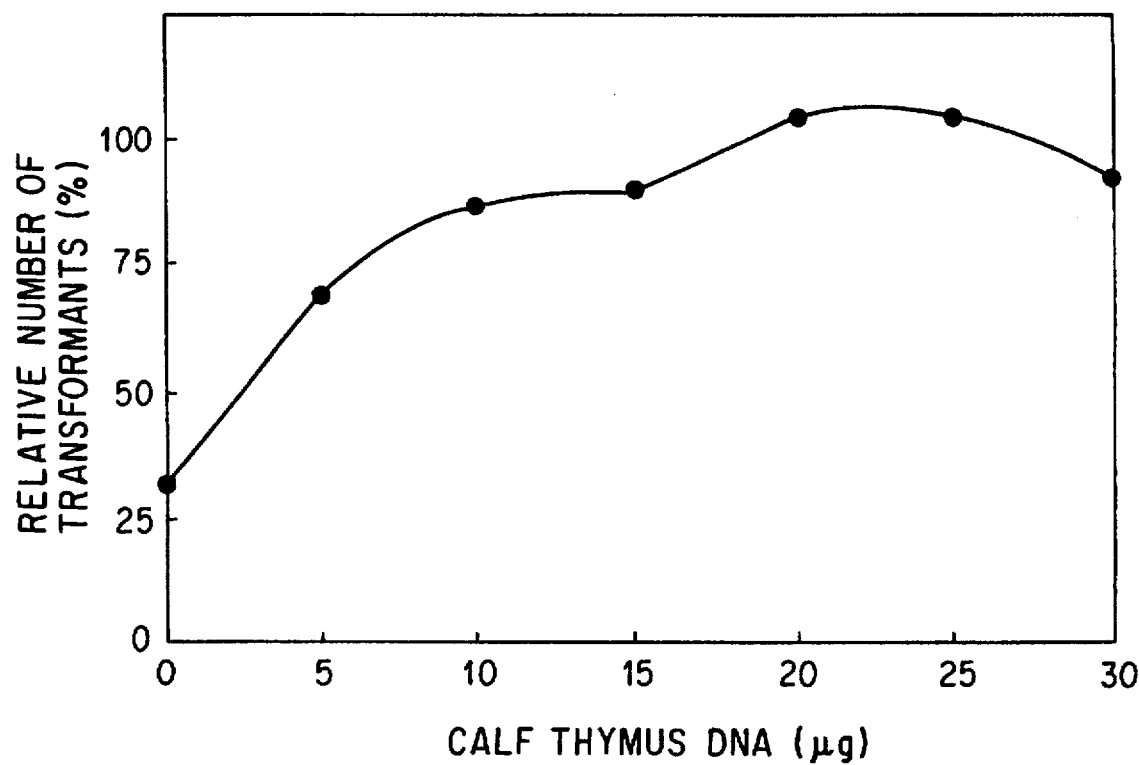

Concentrations of plasmid DNA higher than about 1 μg per transformation reaction were required to obtain good transformation efficiencies and saturation of the transformation reaction was obtained by using 2 μg of plasmid DNA (FIG. 2C). The concentration of calf thymus DNA used as a carrier was not very important although the transformation efficiency decreased when the amount used was higher than 25 μg per reaction (FIG. 2D). Using the optimized transformation conditions, efficiencies of approximately 1 to $7 \times 10^5$ transformants/μg of DNA were routinely obtained.

EXAMPLE 6

Isolation of a stable deleted plasmid from N. lactamdurans pRL1 was relatively unstable in N. lactamdurans. About 70–75% of the transformants obtained with pRL1 isolated from E. coli JM110 showed a deleted plasmid of about 6.0 kb. A similar proportion (about 80%) of the transformants obtained with plasmid pRL1 isolated for E. coli DH5α also yielded the same deleted plasmid.

One of the deleted plasmids, named pULVK1, was mapped in detail by restriction analysis (FIG. 3). A region of 4.0 kb of pRL1 has been deleted (FIG. 3). The deleted plasmid pULVK1 retained the origins of replication of E. coli, and Amycolatoposis sp, and the kanamycin resistance marker. Plasmid pULVK1 was stable and could be propagated in either E. coli or Nocardia lactamdurans and has been routinely used in cloning experiments. It has an approximate copy number of 20–30 copies/cell.

DNA fragments ranging from about 2–10 kb were successfully cloned in the polylinker sites without affecting the stability of the plasmid.

EXAMPLE 7

Development of improved cloning vectors

Figure 4:
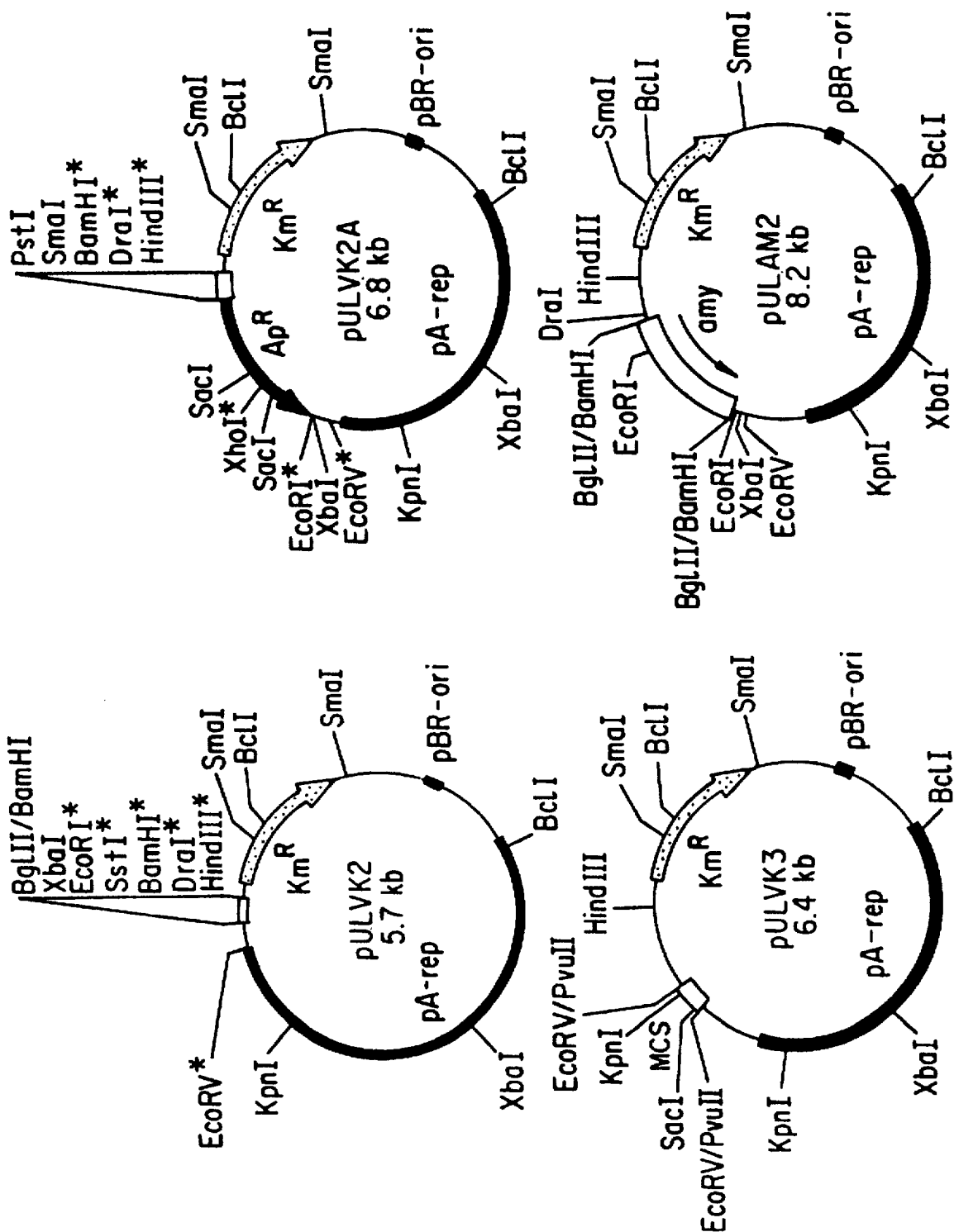
FIG. 4 Improved plasmids for transformation of N. lactamdurans. pULVK2 carries a synthetic polylinker with several unique restriction sites (indicated by asterisks); pULVK3 carries the multiple cloning site from phage M13; pULVK2A contains the apramycin resistance gene ($Am^R$) in addition to the kanamycin resistance gene ($Km^R$), and pULAM2 carries the α-amylase gene (amy) of Streptomyces griseus; all these plasmids have the origin of replication of pA387 of Amycolatopsis sp (pA-rep) and the origin of replication of pBR322 (pBR-ori); the S. griseus DNA fragment in pULAM2 containing the amy gene is indicated by double line.

New improved cloning vectors were developed by replacing the EcoRV-HindIII fragment of pULVK1 with a synthetic linker with several cloning sites (EcoRV, DraI, BamHI, SacI, EcoRI, XbaI and SstI) resulting in plasmid pUVK2 (5.5 kb) (FIG. 4). In a different strategy the multiple cloning site of pBluescript KS(+) was subcloned as a 0.45 kb PvuII fragment. The resulting plasmid, pULVK3, has a size of 6.4 kb (FIG. 4). These plasmids can be easily isolated from N. lactamdurans using the alkaline SDS-lysis method of plasmid isolation from Streptomyces (Kieser, 1984 Plasmid, L12, pp. 19–36).

Construction of vectors with two markers

The apramycin resistance gene was isolated as a 1.2 kb EcoRI-PstI fragment from cosmid pKC505, cloned in the EcoRI-PstI sites of pU2921 [Janssen and Bibb, 1993, Gene, 124, pp. 133–134] and subcloned as a EcoRI-BamHI fragment into pULVK2 yielding plasmid pULVK2A (FIG. 4).

A different marker was introduced at the BamHI site of pULVK2 by inserting the amy gene of Streptomyces griseus from pULVK2 which is efficiently expressed in N. lactamdurans. The new vector with the kan and amy markers was named pULAM2 (FIG. 4). Clones of N. lactamdurans transformed with pULAM2 were easily detected in starch based minimal medium due to the surrounding halo of degradation of starch when exposed to iodine vapors.

By replacing the HindIII-EcoRV fragment of pULVK1 by the 4.4 kb HindIII-EcoRV region of pIJ699 [Kieser and Melton, 1988, Gene, 65, pp. 83–91] containing the origin of replication of S. lividans pIJ101 [Kieser et al., 1982, Mol. Gen. Genet., 185, pp. 223–228], a new multifunctional vector pULVKT3 able to replicate in E. coli N. lactamdurans and several Streptomyces species was obtained, using the kanamycin resistance gene as selective marker in the three microorganisms.

pULVKT3 was used successfully to transform S. clavuligerus and still retains the E. coli DNA fragment unlike other Streptomyces plasmids such as pIJ699 in which the E. coli part is deleted when introduced in S. calvuligerus. The multifinctional vector pULVKT3 is useful to transfer directly cephamycin biosynthetic genes from N. lactamdurans to S. clavuligerus and vice versa.

Promoter probe vectors

Figure 5:
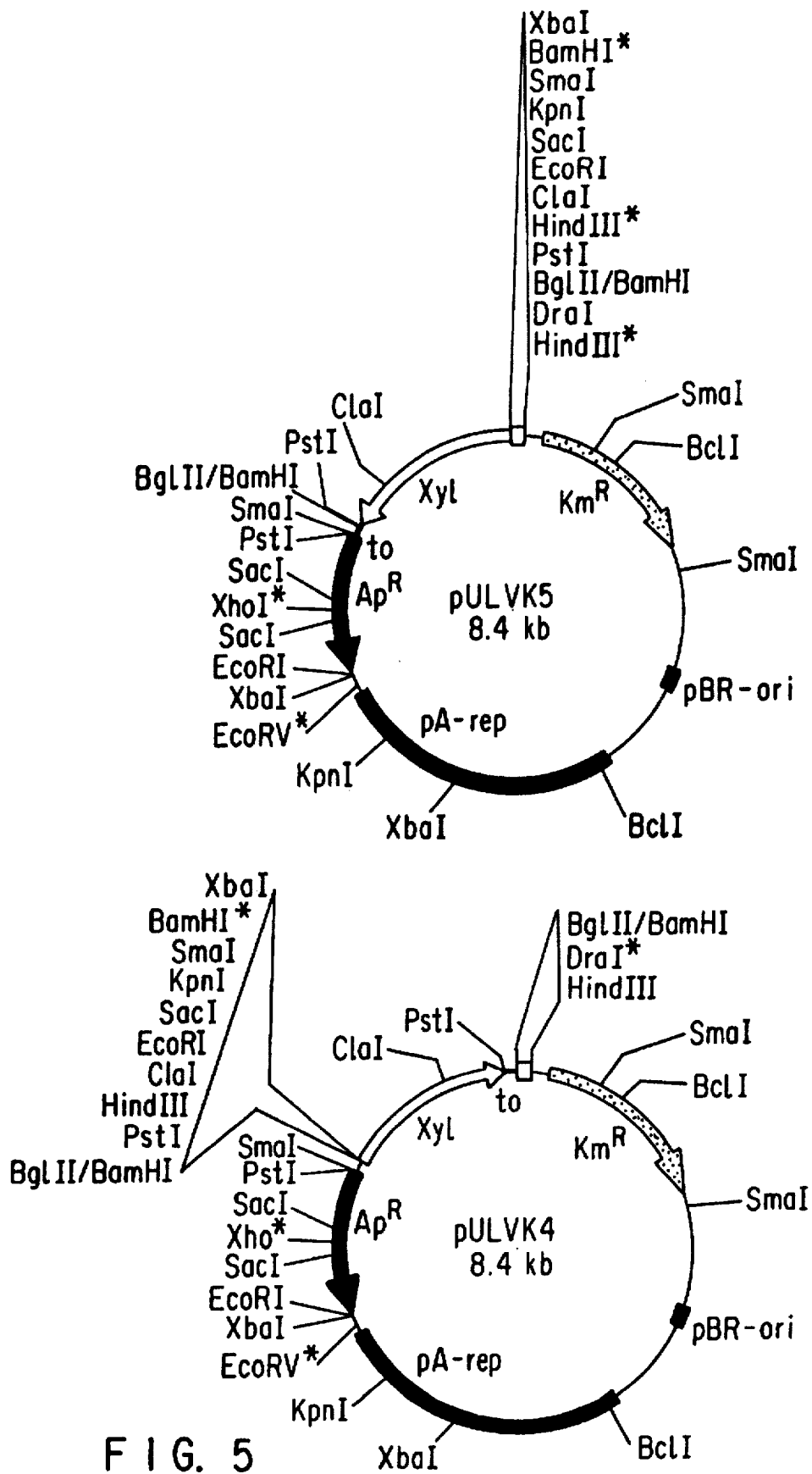
FIG. 5 Promoter-probe plasmids pULVK4 and pULVK5 containing the promoterless xy1E from Pseudomonas putida in addition to the apramycin ($Am^R$) and kanamycin ($Km^R$) resistance genes with the origins of replication pA-rep and pBR-ori as shown in FIG. 4.

The promoter-less xylE of Pseudomonas putida was subcloned as a 1.5 kb BglII fragment from the Streptomyces promoter-probe vector pIJ14083 [Clayton and Bibb, 1990, Nucl. Acids Res., 18, pp. 1077] in both orientations in the BamHI site of pULVK2A yielding the 8.4 kb promoter probe vectors pULVK4 and pULVK5 (FIG. 5).

The usefulness of these vectors was confirmed by subcloning the lat gene promoter of the cephamycin cluster (Coque et al., 1991 J. Bacteriol., 173, pp. 6258–6264) as a HindIII-BamHI fragment in pULVK5 and observing the formation of yellow color in presence of catechol (0.5%). In random cloning of fragments containing promoters it is advisable to replicate the transformants into either MEY or a minimal medium before testing for the yellow color, to avoid the interference of the pink pigment produced by N. lactamdurans in complex media. A minimal medium containing isoleucine as the sole carbon source was found to be the best since in this medium N. lactamdurans grows as white colonies and the yellow color formation after spraying with catechol was easily observed.

What is claimed is:

1. A method for transforming DNA into mycelia of a host strain of *Nocardia lactamdurans* at high efficiency comprising the steps:
   (a) culturing *Nocardia lactamdurans* to exponential growth phase;
   (b) harvesting the mycelia;
   (c) incubating the mycelia in a DNA transformation mixture, the mixture comprising 0.4M to 1.2 M CsCl, 0.075M to 0.125M $MgCl_2$, 30% to 50% PEG of an approximate molecular weight 1000, and at least 0.6 mcg plasmid DNA, to form transformed strains of *Nocardia lactamdurans*; and
   (d) culturing the transformed strains in a medium containing a selection agent.

2. A method for transforming DNA into mycelia of a host strain of *Nocardia lactamdurans* at high efficiency comprising the steps:
   (a) culturing *Nocardia lactamdurans* to exponential growth phase;
   (b) harvesting the mycelia;
   (c) incubating the mycelia in a DNA transformation mixture to form transformed strains of *Nocardia lactamdurans*, wherein the mixture comprises 0.4M to 1.2M CsCl, 0.075M to 0.125M $MgCl_2$, 30% to 50% PEG of an approximate molecular weight 1000, and at least 0.6 mcg plasmid DNA, and wherein the plasmid DNA is selected from pULVK1, pULVK2, pULVK2A, pULVK3, pULVK4, pULVK5 and pULAM2; and
   (d) culturing the transformed strains in a medium containing a selection agent.

3. An isolated strain of *Nocardia lactamdurans* transformed by the method of claim 2.

4. A *Nocardia lactamdurans* transformed with plasmid DNA selected from the group consisting of pULVK1, pULVK2, pULVK2A, pULVK3, pULVK4, pULVK5 and pULAM2.

* * * * *